United States Patent
Baumgaertel

(10) Patent No.: US 9,880,134 B2
(45) Date of Patent: Jan. 30, 2018

(54) METHOD FOR REGISTERING AT LEAST ONE DAMAGE EVENT ON A GLASS SURFACE

(71) Applicant: Hella KGaA Hueck & Co., Lippstadt (DE)

(72) Inventor: Klaas Hauke Baumgaertel, Delmenhorst (DE)

(73) Assignee: HELLA KGAA HUECK & CO., Lippstadt (DE)

( * ) Notice: Subject to any disclaimer, the term of this patent is extended or adjusted under 35 U.S.C. 154(b) by 0 days.

(21) Appl. No.: 15/054,974

(22) Filed: Feb. 26, 2016

(65) Prior Publication Data
US 2016/0253850 A1    Sep. 1, 2016

(30) Foreign Application Priority Data

Feb. 28, 2015    (DE) .......................... 10 2015 002 660

(51) Int. Cl.
| | | |
|---|---|---|
| G07C 5/08 | (2006.01) | |
| G10L 25/21 | (2013.01) | |
| G10L 25/48 | (2013.01) | |
| B60Q 9/00 | (2006.01) | |
| G01N 29/04 | (2006.01) | |
| G01N 29/44 | (2006.01) | |
| B60C 9/00 | (2006.01) | |
| G01N 29/14 | (2006.01) | |
| G01N 29/42 | (2006.01) | |

(52) U.S. Cl.
CPC .............. *G01N 29/44* (2013.01); *B60C 9/00* (2013.01); *G01N 29/14* (2013.01); *G01N 29/42* (2013.01); *G01N 29/4454* (2013.01); *G01N 2291/0232* (2013.01); *G01N 2291/0289* (2013.01)

(58) Field of Classification Search
CPC ........ G01N 29/44; G01N 29/14; G01N 29/42; G01N 29/4454; G01N 2291/0289; G01N 2291/0232; B60Q 9/00
USPC ......................................................... 701/33.9
See application file for complete search history.

(56) References Cited

U.S. PATENT DOCUMENTS

| | | | | |
|---|---|---|---|---|
| 2014/0320298 A1* | 10/2014 | Meiksin | ................ | G01N 29/14 340/683 |
| 2015/0091718 A1 | 4/2015 | Niemann et al. | | |

FOREIGN PATENT DOCUMENTS

| | | |
|---|---|---|
| DE | 102004049380 A1 | 4/2006 |
| DE | 102014013472 A1 | 4/2015 |

(Continued)

*Primary Examiner* — Brian P Sweeney
(74) *Attorney, Agent, or Firm* — Muncy, Geissler, Olds & Lowe, P.C.

(57) ABSTRACT

In a method for registering at least one damage event on a glass surface, particularly a windscreen of a motor vehicle, wherein at least one structure-borne sound signal is registered by a sensor device and the registered structure-borne sound signal is forwarded to at least one analysis unit, it is provided as essential to the invention that a first signal component of the registered structure-borne sound signal is analyzed, that further analysis is not begun until a first amplitude of the registered structure-borne sound signal has decayed, that the curve of the registered structure-borne sound signal is examined for the existence of signal jumps, and that conclusions may be drawn regarding at least one damage incident on the glass surface from the existend of at least one signal jump.

15 Claims, 2 Drawing Sheets

(56) References Cited

FOREIGN PATENT DOCUMENTS

JP          10326385  A      12/1998
JP        2003247986  A   *   9/2003

* cited by examiner

METHOD FOR REGISTERING AT LEAST ONE DAMAGE EVENT ON A GLASS SURFACE

BACKGROUND OF THE INVENTION

Field of the Invention

The invention relates to a method for registering at least one damage event on a glass surface, particularly a windscreen of a motor vehicle, wherein at least one structure-borne sound signal is registered by a sensor device, and the registered structure-borne sound signal is forwarded to at least one analysis unit.

Brief Discussion of the Related Art

Devices and methods for registering damage events are known, and are used in passenger protection systems in motor vehicles, for example. A vehicle sensor provided for registering vibrations in frequency ranges that may be due to mechanical vibration, among other causes is described in DE 10 2004 049 380 A1, for example. In this case, the vehicle sensor has a processing characteristic for electrical signals that are generated by the registering of various vibrations. The processing characteristic may be adjusted used a control signal. The vehicle sensor may also be used to detect material damage, such as breakage of glass.

A disadvantage of the known devices and methods it that no provisions are made for differentiating between the types of damage the glass surface has suffered. For example, there are no provisions for determining whether detected damage to a windscreen was caused by spalling or a crack in the windscreen, which necessitates immediate repair.

SUMMARY OF THE INVENTION

The object underlying the invention is to suggest a method for registering a damage event on a glass surface, which makes it possible to make distinctions between the nature and severity of the damage.

The solution to object is provided with a method having the features of claim 1. Refinements and advantageous variations are described in the respective subordinate claims.

In a method for registering at least one damage event on a glass surface, particularly on a windscreen of e motor vehicle, wherein at least one structure-borne sound signal is registered by a sensor device and the registered structure-borne sound signal is forwarded to at least one analysis unit, it is provided as essential for the purposes of the invention that a first signal component of the registered structure-borne sound signal is analysed, the analysis is not begun until a first amplitude of the registered structure-borne sound signal has decayed, that the curve of the registered structure-borne sound signal is examined for the existence of signal jumps, and that the existence of at least one signal jump is taken to suggest at least one damage to the glass surface.

A glass surface in a vehicle—particularly the windscreen of a motor vehicle—may begin vibrating and consequently suffer damage through contact with a hard body, such as a stone. In the event of an impact that does not cause damage, the glass surface may be caused to vibrate in a linear-elastic range. This means that a structure-borne sound signal is generated on the glass surface, the amplitude of which can be attenuated continuously. In order to absorb the structure-borne signal, a piezoelectric film may particularly be used, generating electrical voltage signals in response to extensions and compressions, wherein the voltage signals generated by the piezoelectric film are proportional to the expanse of the glass pane. In an impact event—for example impact from a stone—that does cause damage, cracks or spalling may occur in the glass, for example. In the event of cracks or spalling, the glass is subjected to stress locally which exceeds its yield strength, and consequently the mechanical tension in the glass is reduced abruptly. This abrupt change in the mechanical tension in the glass is rendered visible as signal jumps in the measurement signals that are recorded by the piezoelectric foil. The existence of a signal jump in the detected structure-borne thus suggests that the glass surface has suffered some damage. In order to detect signal jumps, particularly the graph of the registered structure-borne sound signal is examined with an analysis unit. In the registered structure-borne sound signal, a first signal component, particularly the amplitude of the first signal component is analysed before the actual analysis is begun. The first signal component usually relates to the shock wave, which is caused by the impact of a body on the glass surface of the motor vehicle for example. This impact may cause the glass to break, for example. By analysing the structure-borne sound signal component after the amplitude of the first signal component has decayed, particularly by registering the signal jumps in the signal component after the first amplitude, has decayed, it s possible to determine not only breaks or cracks in the glass surface, but also damage that only affects the surface, such as spalling. The decay of a first amplitude may be deferred by introducing a delay element, with which it is possible to analyse the captured signal only after a certain time lag.

In a refinement of the method, the number of signal jumps is determined, and a conclusion is drawn regarding the nature of the damage from the number of signal jumps. For example, the number of signal jumps in a detected signal in a defined time, particularly a defined time after a first impact, can be counted. The larger the number of signal jumps, the more severe the damage is to the glass surface that is being observed.

In an refinement of the method, a number of signal jumps less than or equal to 80 indicates minor damage and a number of signal jumps greater than 80 indicates serious damage to the glass surface, in particular, minor damage is suggested for a number from 1 to 80 signal jumps, and serious damage is suggested for a number from 81 to 300 signal jumps. The severity of the damage to the glass surface under consideration is determined on the basis of the number of signal jumps in a given time interval after the decay of the amplitude of the first signal component, for example. Below a number of 80 signal jumps, for example, slight spalling of the glass surface may be concluded, whereas a number of signal jumps above 80 suggests severe damage, such as a crack in the glass surface under consideration. For example, a detected number of 26 signal jumps may suggest minor spalling of the glass surface under consideration, whereas a detected number of 120 signal jumps suggests a crack in the glass surface under consideration. Moreover, even finer distinctions can be chosen, wherein corresponding graduations may be set individually.

In a further refinement of the method, the strength of the signal jumps is included for the purpose of determining the nature of the damage. In this context, the detected structure-borne sound signal that results from an impact event with serious damage to the glass surface has larger signal jumps than a structure-borne sound signal, that results from less severe damage.

In a refinement of the method, a high pass filter suppressing all frequencies in the recorded structure-borne sound signal that are below a limit frequency is applied to the structure-borne sound signal before the curve of the structure-borne sound signal is analysed. The limit frequency may be 10 kHz for example. By suppressing the frequency components of the structure-borne sound signal that are below this limit frequency, the frequency components that are attributable to travel noise and/or elastic vibration components are filtered out of the structure-borne sound signal spectrum. This filtering thus ensure that the frequencies in the signal that is to be further analysed are attributable to an impact or contact event on the glass surface under consideration, and the signal for analysis is not distorted by extraneous frequency components. After the high pass filtering of the registered structure-borne sound signal, only the signal jumps in the frequency spectrum remain.

In an advantageous refinement of the method, the frequencies below a limit frequency are suppressed by an RC circuit, and the capacitance of the RC circuit is determined by the structure-borne sensor. The structure-borne sensor is preferably a piezoelectric foil that has a capacitance C. Resistance R may be established for example by the input resistance of the sensor circuit. In this way, an RC circuit that functions as a high pass filter is thus created integrating a piezoelectric foil in the sensor circuit, without the need for additional components or switching elements.

In a refinement of the method, the structure-borne sound signal that has passed through the high-pass filter is rectified, and only positive voltage components are forwarded for further analysis. Various types of rectifiers can be used to rectify the structure-borne sound signal. Rectification of the structure-borne sound signal that has passed through the high-pass filter is particularly advantageous, because after it has been rectified only positive voltage components of the structure-borne sound signal are forwarded for further analysis. The negative voltage components do not contain any information of significance for the analysis. Accordingly further electronic components that would be required to analyse the negative voltage components, that is to say the negative half-cycle, may be dispensed with. This results in reduction in the cost of the circuit arrangement.

In a refinement of the method, the envelope curve of the rectified signal is determined. In particular, the amplitude envelope curve of the signal is determined. The calculation of the amplitude envelope curve enables a simple analysis of the signal jump.

In an advantageous refinement of the method, the envelope curve is determined by low pass filtering. In low pass filtering, signals above a limit frequency are suppressed. The limit frequency may be 100 kHz for example. Low pass filtering of the signal may be used to suppress high-frequency interference. It is also possible for individual signal peaks that are caused for example by microcracks in the glass surface under consideration to be stretched. This makes it easier to process and analyse the signal further.

In a refinement of the method, the analysis unit is switched from an energy saving state into a ready state when a structure-borne sound signal is registered. Preferably a piezoelectric foil serves as the structure-borne sensor. When it is deflected, for example by a structure-borne sound signal, a piezoelectric foil produces an electrical voltage on the glass surface under consideration. When an electrical voltage is output by the piezoelectric foil, that is to say when a structure-borne sound signal occurs, the analysis unit may be switched from an energy saving state into a ready mode. The analysis unit, which may have the form of a microcontroller, for example, is only needed when a corresponding structure-borne sound signal is to be analysed. In time segments in which no structure-borne activity is detected, the analysis unit remains in an energy saving state to enhance the energy efficiency of the sensor device. If the analysis unit remained in a ready state permanently, the electrical energy required by the analysis unit would be consumed needlessly.

In a refinement of the method, the amplitude of the envelope curve is calculated, the amplitude of the envelope curve is compared with another amplitude threshold value, and when the calculated amplitude exceeds the amplitude threshold value, the analysis unit is switched from an energy saving state to a ready state. By calculating the amplitude of the envelope curve and comparing it with a previously established amplitude threshold value, it is possible to determine whether the detected structure-borne sound signal is a structure-borne sound signal that is attributable to an impact event, which has a greater amplitude than a structure-borne sound signal caused by standard operation, for example. If a structure-borne sound signal that is attributable to an impact event is detected, the analysis unit can be switched into a ready state, so that the detected structure-borne sound signal can be analysed by the analysis unit, for example, for the existence of signal jumps.

In a refinement of the method, the number of signal jumps in a predefined time interval is calculated when a second amplitude threshold value is exceeded by an amplitude of the envelope curve. The second amplitude threshold value may serve example to determine whether the detected structure-borne sound signal, which can be attributed to an impact event because the first amplitude threshold value was exceeded, is a structure-borne sound signal that is caused by damage to the glass surface under consideration, or if the structure-borne sound signal is attributable to an impact event that causes elastic vibration in the glass surface under consideration. For example, the amplitude of the envelope curve of a structure-borne sound signal that is attributable to a damaging impact can have a greater amplitude than a structure-borne sound signal that is attributable to a non-damaging impact. In a time interval, for example a period of 100 milliseconds after the first impact, signal jumps in the captured structure-borne sound signal can be detected by the analysis unit, in the form of a microcontroller or analogue electronic circuit, for example. If no signal jumps are detected, the impact event may be considered non-damaging. The more jumps that are detected, the more severe is the damage caused by the impact event. For example, for minor spalling of the glass surface under consideration, 26 signal jumps may be detected in the predetermined time frame, whereas 120 signal jumps can be detected if a window is broken.

In an advantageous refinement of the method, a warning signal is output after a damage event is registered. For example, a warning signal corresponding to the severity of the damage may be put out, reporting the existence of damage to the glass surface under consideration, and the severity of the damage. For example, if a windscreen of a motor vehicle has cracked, an urgent instruction may be issued to the vehicle user to have the damage repaired as soon as possible, in order to avoid endangering the vehicle passengers. The warning signal may be an acoustic and/or optical signal, for example, which is output to the vehicle users via a display and/or loudspeaker system.

BRIEF DESCRIPTION OF THE DRAWINGS

In the following, the invention will be explained in greater detail with reference to a preferred embodiment thereof, represented in the drawing. In detail, the figures of the drawing represent schematically.

DETAILED DESCRIPTION OF THE PREFERRED EMBODIMENTS

Figure 1:
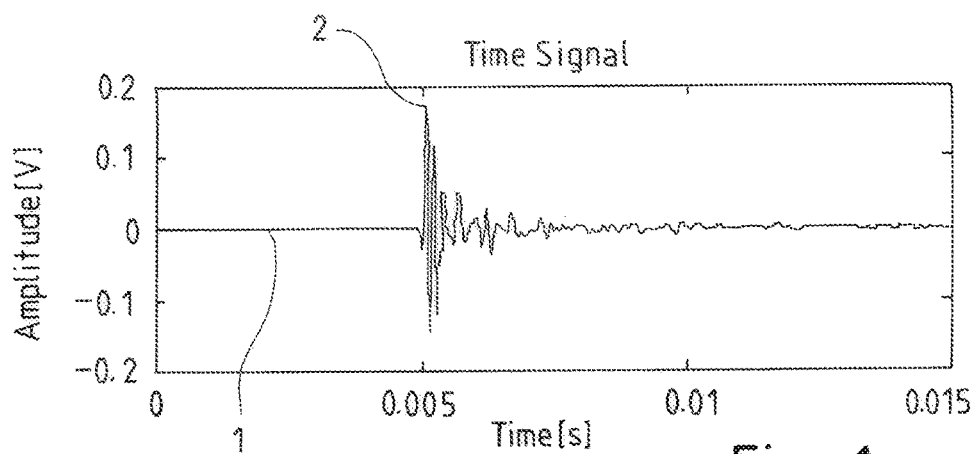
FIG. 1 a plot of a structure-borne sound signal that is attributable to an impact without damage.

FIG. 1 represents an exemplary structure-borne sound signal 1 that is attributable to an impact event that causes no damage to a windscreen. The impact gives rise to a first signal amplitude 2, which then attenuates continuously. Accordingly, the windscreen vibrates in a linear-elastic range.

Figure 2:
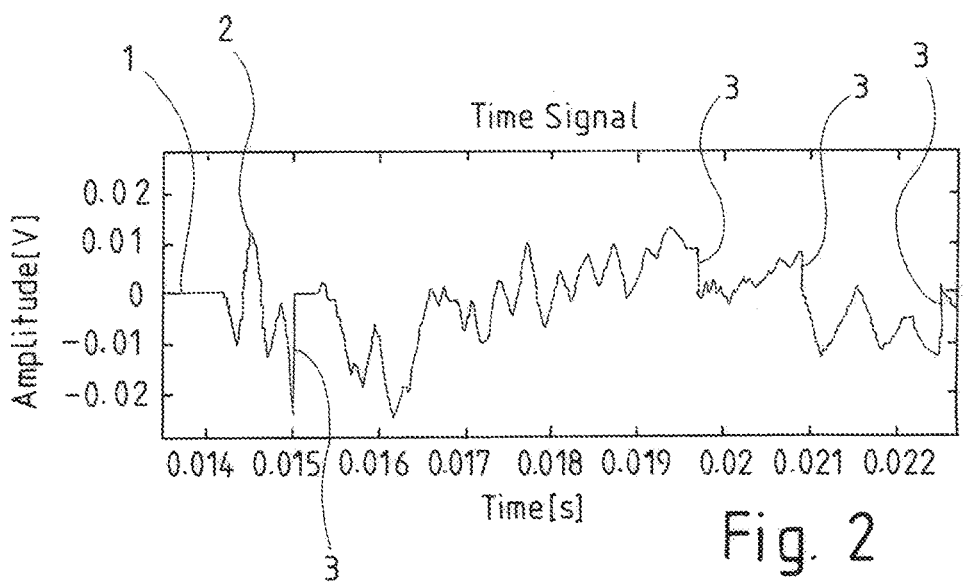
FIG. 2 a plot of a structure-borne sound signal that is attributable to an impact with minor damage.

FIG. 2 represents the discontinuous signal curve of a structure-borne sound signal 1 that is attributable to an impact on a windscreen with minor damage. The number of signal jumps 3 provides an indication that there is minor damage to the windscreen. The first signal amplitude 2 of the first signal component in the detected structure-borne sound signal 1 is attributed to the impact, by a body on the glass surface under consideration, for example. Signal amplitude 2 is not used for classifying the damage event. The analysis of structure-borne sound signal 1, particularly registering the signal jumps 3, takes place in the portion of the structure-borne sound signal 1, in which first signal amplitude 2 has decayed.

Figure 3:
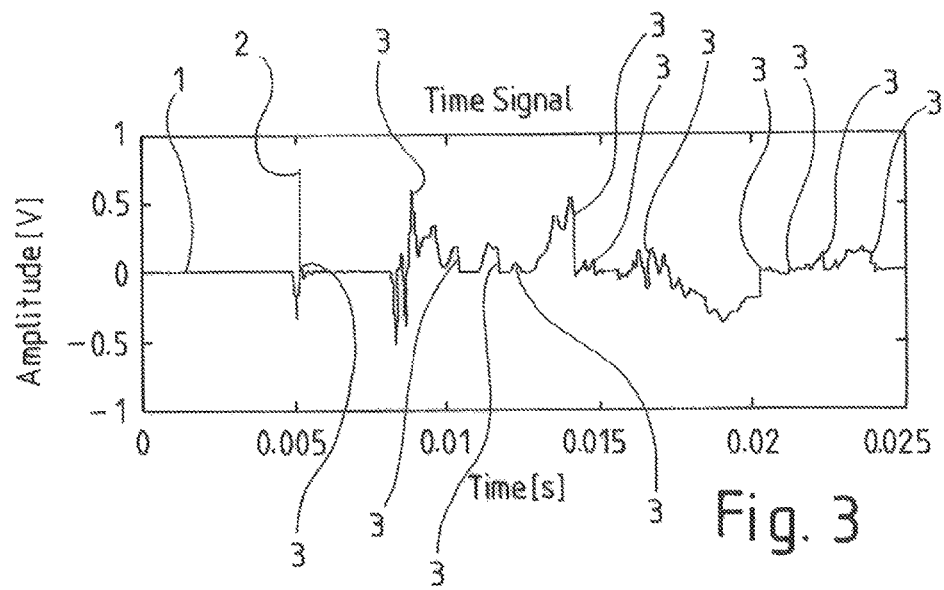
FIG. 3 a plot of a structure-borne sound signal that is attributable to an impact with severe damage.

FIG. 3 shows the discontinuous signal curve of a structure-borne sound signal 1, that is attributable to an impact with severe damage to the windscreen. The number of signal jumps 3 provides an indication of the severity of the damage. Compared with the signal curve shown in FIG. 2, significantly more signal jumps are clearly evident.

Figure 4:
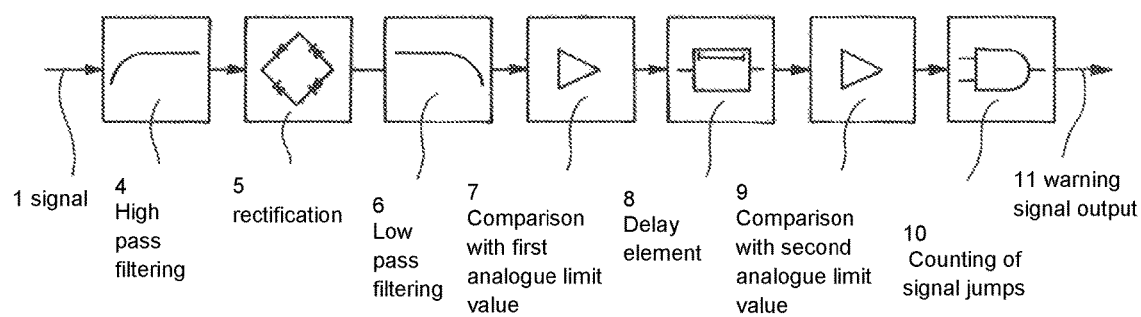
FIG. 4 a block diagram of the algorithm for registering a damage event.

FIG. 4 shows a block diagram of the steps of the method for registering a damage event to a glass surface. The signal 1 caused by an impact event on the glass surface is passed through a high pass filtering 4, with a limit frequency of 10 kHz for example. The high pass filtering 4 suppresses the frequencies that are caused by normal driving operation, for example, due to elastic vibration components. After passing through the high pass filter, the signal is forwarded to a rectifier 5, by which the negative voltage components are removed. Analysis of a purely positive voltage signal is more cost-efficient, because fewer electronic components are needed for this. The rectified signal is passed through an analogue low pass filtering 6, with a limit frequency of 100 kHz for example. This suppresses high frequency interference. The preparation of an envelope curve of the signal simplifies the subsequent further signal analysis. The amplitude of the envelope is calculated, and this amplitude is compared with a first analogue limit value 7. This comparison with a first analogue limit value 7 enables a structure-borne sound signal caused by normal driving operation, for example, to be distinguished from the structure-borne sound signals that are due to impact events, for example. When a structure-borne sound signal that is attributable to an impact event is registered, that is to say when the first amplitude limit value 7 is exceeded by the amplitude of the detected structure-borne sound signal, the analysis unit is switched from an energy saving state to a ready state. A delay element 8 may serve to insert a lag period into the method sequence until the first amplitude of the detected structure-borne sound signal has decayed. The comparison of amplitude 2 of the envelope curve with a second amplitude threshold value 9 may help to distinguish between a structure-borne sound signal that is attributable to a event damaging a glass surface and structure-borne sound signal that is caused by vibration of the glass surface under consideration. After a comparison of the amplitude of the envelope curve with the second amplitude threshold value 9, for example, the signal jumps 3 in the registered signal 10 may be counted in a time frame of 100 milliseconds after the first impact, for example. A warning signal 11 may be output or not, depending on the number of signal jumps 3 in the time frame. If no signal jumps are detected in the time frame, a warning signal can be dispensed with. A large number of signal jumps 3 implies severe damage to the glass surface, a broken windscreen for example. The warning signal 11 may be output to a vehicle user, for example, depending on the severity of the damage.

All of the features explained in the preceding description and in the claims can be combined in any permutation with the features of the independent claim. The disclosure of the invention is thus not limited to the described and claims combinations of features, but rather all feature combinations that are practical within the scope of the invention are to be considered disclosed.

The invention claimed is:

1. A method for registering at least one damage event on a glass surface, comprising:
    registering at least one structure-borne sound signal by a sensor device,
    forwarding the registered structure-borne sound signal to at least one analysis unit,
    analyzing a first signal component of the registered structure-borne sound signal,
    delaying the analysis until a first amplitude of the registered structure-borne signal has decayed, wherein the delaying is accomplished by a delay element inserting a lag period,
    examining the curve of the registered structure-borne signal for the existence of signal jumps, and
    determining at least one damage to the glass surface by the existence of at least one signal jump.

2. The method according to claim 1, wherein the number of signal jumps is calculated and that a conclusion is drawn regarding the nature of the damage from the number of signal jumps.

3. The method according to claim 2, wherein a number of signal jumps less than or equal to 80 indicates minor damage and a number of signal jumps greater than 80 indicates serious damage to the glass surface.

4. The method according to claim 3, wherein minor damage is suggested for a number from 1 to 80 signal jumps, and serious damage is suggested for a number from 81 to 300 signal jumps.

5. The method according to claim 1, wherein magnitude of the signal jumps is considered in the determination of the nature of the damage.

6. The method according to claim 1, wherein a high pass filter suppressing all frequencies in the recorded structure-borne signal that are below a limit frequency is applied to the structure-borne signal before the curve of the structure-borne signal is analysed.

7. The method according to claim 6, wherein the frequencies below the limit frequency are suppressed by an RC circuit, and that the capacitance of the RC circuit is determined by the structure-borne sensor.

8. The method according to claim 6, wherein the structure-borne signal having passed through the high pass filter undergoes rectification, and that only positive voltage components are forwarded for further analysis.

9. The method according to claim 8, wherein the envelope curve of the rectified signal is calculated.

10. The method according to claim 9, wherein the envelope curve is calculated by low pass filtering.

11. The method according to claim 9, wherein the amplitude of the envelope curve is calculated, the amplitude of the envelope curve is compared with an amplitude threshold value, and when the calculated amplitude exceeds the amplitude threshold value, the analysis unit is switched from an energy saving state to a ready state.

12. The method according to claim 9, wherein the number of signal jumps in a predefined time interval is calculated when a second amplitude threshold value is exceeded by an amplitude of the envelope curve.

13. The method according to claim 1, wherein the analysis unit is switched from an energy saving state into a ready state when a structure-borne signal is registered.

14. The method according to claim 1, wherein a warning signal is output after a damage event.

15. The method according to claim 1, wherein the glass surface is a windscreen of a motor vehicle.

* * * * *